United States Patent
Manneck et al.

(10) Patent No.: US 10,987,291 B2
(45) Date of Patent: *Apr. 27, 2021

(54) GENTLE AGENTS AND METHODS FOR OXIDATIVE DYEING USING SELECTED DICARBOXYLIC ACIDS

(71) Applicant: Henkel AG & Co. KGaA, Duesseldorf (DE)

(72) Inventors: Hartmut Manneck, Barnitz (DE); Thomas Hippe, Appen (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 177 days.

This patent is subject to a terminal disclaimer.

(21) Appl. No.: 16/305,621

(22) PCT Filed: May 31, 2017

(86) PCT No.: PCT/EP2017/063161
§ 371 (c)(1),
(2) Date: Nov. 29, 2018

(87) PCT Pub. No.: WO2017/207631
PCT Pub. Date: Dec. 7, 2017

(65) Prior Publication Data
US 2020/0330348 A1    Oct. 22, 2020

(30) Foreign Application Priority Data

May 31, 2016 (DE) .................... 10 2016 209 468.8

(51) Int. Cl.
| | | |
|---|---|---|
| *A61Q 5/10* | (2006.01) | |
| *A61K 8/362* | (2006.01) | |
| *A61K 8/22* | (2006.01) | |
| *A61K 8/25* | (2006.01) | |
| *A61K 8/365* | (2006.01) | |
| *A61K 8/41* | (2006.01) | |
| *A61K 8/44* | (2006.01) | |
| *A61K 8/46* | (2006.01) | |
| *A61K 8/81* | (2006.01) | |
| *A61Q 5/08* | (2006.01) | |
| *A61K 8/49* | (2006.01) | |

(52) U.S. Cl.
CPC ............... *A61K 8/362* (2013.01); *A61K 8/22* (2013.01); *A61K 8/25* (2013.01); *A61K 8/365* (2013.01); *A61K 8/41* (2013.01); *A61K 8/44* (2013.01); *A61K 8/447* (2013.01); *A61K 8/463* (2013.01); *A61K 8/466* (2013.01); *A61K 8/4913* (2013.01); *A61K 8/8182* (2013.01); *A61Q 5/08* (2013.01); *A61Q 5/10* (2013.01); *A61K 2800/4322* (2013.01); *A61K 2800/4324* (2013.01); *A61K 2800/59* (2013.01); *A61K 2800/882* (2013.01)

(58) Field of Classification Search
CPC ... A61Q 5/10; A61K 8/22; A61K 8/41; A61K 2800/4324; A61K 8/44; A61K 8/365; A61K 8/23; A61K 8/361; A61K 8/447; A61K 8/362
USPC .......................................................... 8/405
See application file for complete search history.

(56) References Cited

U.S. PATENT DOCUMENTS

| | | | | |
|---|---|---|---|---|
| 5,030,241 | A  * | 7/1991 | Clausen ................... | A61Q 5/10 8/414 |
| 6,515,114 | B1 | 2/2003 | Hanna, Jr. et al. | |
| 8,062,629 | B2 | 11/2011 | Terazaki et al. | |
| 9,980,891 | B2 * | 5/2018 | Manneck .................. | A61K 8/36 |
| 9,993,406 | B2 * | 6/2018 | Manneck ............... | A61K 8/415 |
| 10,143,646 | B2 * | 12/2018 | Hippe ...................... | A61Q 5/08 |
| 10,293,191 | B2 * | 5/2019 | Kerl .......................... | A61K 8/22 |
| 2002/0189034 | A1 * | 12/2002 | Kitabata .................. | A61K 8/22 8/405 |
| 2011/0247644 | A1 | 10/2011 | Oberkobusch et al. | |
| 2015/0053228 | A1 * | 2/2015 | Bonauer .................. | A61Q 5/10 132/208 |

FOREIGN PATENT DOCUMENTS

| | | |
|---|---|---|
| DE | 10051774 A1 | 4/2002 |
| DE | 102015222946 A1 | 5/2017 |
| EP | 0765154 A1 | 4/1997 |
| EP | 1174112 A2 | 1/2002 |
| GB | 1136659 A | 12/1968 |
| GB | 2259717 A | 3/1993 |
| WO | 2005115314 A1 | 12/2005 |
| WO | 2017085117 A1 | 5/2017 |

OTHER PUBLICATIONS

STIC Search Report dated Aug. 24, 2020.*
EPO, International Search Report issued in International Application No. PCT/EP2017/063161, dated Sep. 4, 2017.

* cited by examiner

*Primary Examiner* — Eisa B Elhilo
(74) *Attorney, Agent, or Firm* — Lorenz & Kopf, LLP

(57) ABSTRACT

The present disclosure concerns colouring agents for keratinous fibres, in particular for human hair, which—with respect to its weight—contain at least one compound selected from the group formed by oxidative dye precursors, direct dyes and mixtures thereof, from about 0.1 to about 5% by weight of dicarboxylic acid(s) containing from about 2 to about 10 carbon atoms and/or salt(s) of this(these) acid(s), from about 20 to about 95% by weight of water, and less than about 0.1% by weight of peroxy compound(s), to produce oxidative colouring agents with improved protection of fibres.

17 Claims, No Drawings

GENTLE AGENTS AND METHODS FOR OXIDATIVE DYEING USING SELECTED DICARBOXYLIC ACIDS

CROSS-REFERENCE TO RELATED APPLICATION

This application is a U.S. National-Stage entry under 35 U.S.C. § 371 based on International Application No. PCT/EP2017/063161, filed May 31, 2017 which was published under PCT Article 21(2) and which claims priority to German Application No. 10 2016 209 468.8, filed May 31, 2016, which are all hereby incorporated in their entirety by reference.

TECHNICAL FIELD

The present disclosure relates to a hair care agent for the oxidative colouring of hair, as well as to a gentle method for the oxidative colouring of hair, in which keratinous fibres are protected from oxidative influences, or oxidative damage to hair is repaired.

BACKGROUND

During the oxidative colouring of hair, a problem concerning damage to the keratinous fibres can occur due to the aggressive agents employed. In particular, the natural hydrophobic nature of the keratinous fibre is reduced, because the colouring or lightening agent initially has to render the hair capable of being penetrated, so that it can take effect. However, the water-repellent nature on the one hand provides the hair with a natural protection, and on the other hand is closely linked to characteristics which are desirable to the consumer, such as shine, smoothness, feel and "flow" of the hair.

In order to overcome the disadvantages mentioned above, what are known as pre-treatment agents are commercially available which are intended to protect the hair from the aggressive effects. However, they frequently make the hair heavier or have a deleterious influence on the success of the subsequent lightening or colouring of the hair. In particular, the colour fastness to washing could be impaired by the pre-treatment agent. In addition, many post-treatment agents are known; these are used to try and repair the damage to the hair caused by the oxidative colouring treatment. All of these methods, however, demand a multi-step application method, namely an application of a further hair treatment agent either before or after colouring. The consumer often views this as tedious, because the oxidative colouring treatment alone is very time-consuming as it involves several operational steps and a treatment time of up to about 60 minutes.

BRIEF SUMMARY

Colouring agents for keratinous fibres and methods for the oxidative colouring of keratinous fibres are provided herein. In an embodiment, a colouring agent for keratinous fibres, includes—with respect to its weight—
a) at least one compound selected from the group of oxidative dye precursors, direct dyes, and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.1 to about 5% by weight, calculated with respect to the undissociated dicarboxylic acid and with respect to the weight of the colouring agent,
c) from about 20 to about 95% by weight of water, and
d) less than about 0.1% by weight of peroxy compound(s).

In another embodiment, a method for the oxidative colouring of keratinous fibres, includes the following steps
I. preparing a composition (A) comprising
a) at least one compound selected from the group formed by oxidative dye precursors, direct dyes and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.1 to about 5% by weight, respectively calculated with respect to the undissociated dicarboxylic acid and with respect to the weight of the composition (A),
c) from about 20 to about 95% by weight of water, and
d) less than about 0.1% by weight of peroxy compound(s),
II. preparing a composition (B) comprising at least one peroxy compound,
III. mixing the compositions (A) and (B) together, then immediately
IV. applying the mixture of (A) and (B) to the keratinous fibres, and
V. rinsing out after a treatment time of from about 0.1 to about 60 minutes,
VI. optionally, other keratinous fibre treatments chosen from shaping, conditioning and/or drying.

In another embodiment, a colouring agent for keratinous fibres, includes—with respect to its weight—
a) from about 0.05 to about 5% by weight of at least one compound selected from the group of oxidative dye precursors, direct dyes, and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.5 to about 2% by weight, calculated with respect to the undissociated dicarboxylic acid and with respect to the weight of the colouring agent,
c) from about 20 to about 95% by weight of water,
from about 0.2 to 1.2% by weight of at least one amino acid chosen from the group of arginine, lysine, histidine, asparagine, glutamine, cysteine, methionine, tryptophan as well as mixtures thereof,
from about 0.02 to 1.0% by weight of at least one compound with general formula (III)

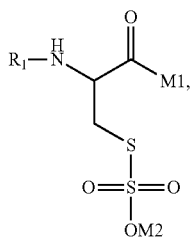

(III)

wherein

R1 represents a hydrogen atom or a structural element with formula (IV)

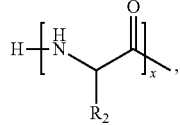

(IV)

wherein x represents a whole number from about 1 to about 100, the residue R2 in each of the structural elements with formula (IV) is respectively selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M1 represents the group —OM2 or a structural element with formula (V)

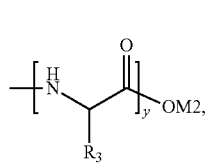

(V)

wherein y represents a whole number from about 1 to about 100, the residue R3 in each of the structural elements with formula (V) is respectively selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, and M2 represents a hydrogen atom, an equivalent of a monovalent or multivalent cation, or an ammonium ion $(NH4)^+$, and from about 1.0 to about 2.3 weight % of at least one polymer A, which comprises at least ten constituent elements with formula (I)

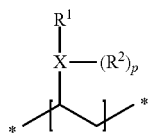

(I)

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are selected from N and O and/or optionally substituted with at least one C1-C6 alkyl group and/or optionally substituted with at least one functional group, and p is equal to about 0 when X represents oxygen and p is equal to about 1 when X represents nitrogen, and wherein the polymer A contains no permanently ionic constituent units, wherein the colouring agent is free from peroxy compounds.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is to provide an agent and a method for oxidative hair colouring with a treatment that protects the hair, which overcomes the disadvantages mentioned above, without having a negative influence on the colour resulting from the oxidative colouring treatment. In this regard, in particular, a colouring agent and a method will be provided, in which the hair is not made heavy and as little damage occurs to the hair as possible. Furthermore, the intended protection of the hair should be carried out rapidly as possible, and as far as possible should be carried out together with the colouring step.

The use of dicarboxylic acids such as succinic acid is known in the hair care art. They are widely used in shampoos and in particular in conditioners in order to provide conditioning effects. In this regard, patent application WO 2005/115314 A1 discloses a method for restructuring keratinous fibres, in which the keratin fibres are brought into contact with cystine and with at least one dicarboxylic acid containing from about 2 to about 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid, and succinic acid is particularly preferred. The patent application DE 10051774 A1 describes the use of short-chain carboxylic acids with a molecular weight of less than about 750 g/mol in cosmetic agents as a substance for the restructuring of keratinous fibres. The patent application EPI174112A discloses hair treatment agents which, in addition to an organic acid, contain an organic solvent, a cationic surfactant and a higher alcohol as further essential components and are used to repair pores in the hair.

Recently, agents have come onto the market which have to be mixed together with colouring compositions for the purposes of protecting the fibres, and which contain dicarboxylic acids. In those agents, however, although a further hair treatment agent is not applied before or after colouring, that agent has to be mixed with the colouring agent per se prior to application, which in fact means a further operational step and the consumer finds that tedious.

It has now been discovered that oxidative colouring agents can be provided which have an improved protection of fibres when the colour cream to be mixed with the developer during preparation by the consumer contains at least one dicarboxylic acid containing from about 2 to about 10 carbon atoms in addition to typical components such as water and dyes or their precursors, and is substantially free from peroxides. This not only means that a further operational step is avoided, but also, these agents, for otherwise identical quantities of dicarboxylic acid(s) that are used, are more effective even than subsequent admixing as regards protection of the fibres.

In a first embodiment, the present disclosure provides colouring agents for keratinous fibres, in particular for human hair, containing—with respect to their weight—
a) at least one compound selected from the group formed by oxidative dye precursors, direct dyes and mixtures thereof,
b) from about 0.1 to about 5% by weight, respectively calculated with respect to the undissociated dicarboxylic acid and with respect to the weight of the colouring agent, of dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this(these) acid(s),
c) from about 20 to about 95% by weight of water, and
d) less than about 0.1% by weight of peroxy compound(s).

In a further aspect, the present disclosure provides a method for the oxidative colouring of keratinous fibres, in particular of human hair, comprising the following steps of the method
I preparing a composition (A) containing—with respect to its weight—
a) at least one compound selected from the group formed by oxidative dye precursors, direct dyes and mixtures thereof,
b) from about 0.1 to about 5% by weight, respectively calculated with respect to the undissociated dicarboxylic acid and with respect to the weight of the composition (A), of dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this(these) acid(s),
c) from about 20 to about 95% by weight of water, and
d) less than about 0.1% by weight of peroxy compound(s)
II. preparing a composition (B) containing at least one peroxy compound, which is preferably hydrogen peroxide, wherein the composition (B) preferably has a pH in the range from about 2.5 to about 6.5, preferably from about 3.0 to about 5.5, particularly preferably from about 3.5 to about 5.0, respectively measured at 20° C.,
III. mixing the compositions (A) and (B) together, then immediately
IV. applying the mixture of (A) and (B) to the keratinous fibres, in particular to the human hair, and
V. rinsing out after a treatment time of from about 0.1 to about 60 minutes, preferably from about 1 to about 45 minutes, particularly preferably from about 10 to about 30 minutes,
VI. if appropriate, other hair treatments such as shaping, conditioning and/or drying.

The agents as contemplated herein or used in the method as contemplated herein preferably contain at least one coupling component. Particularly beautiful colours can be obtained when at least one coupling component is contained in the agents as the coupling component, which is selected from the group formed by 3-amino-2-methylamino-6-methoxypyridine, 3-amino-6-methylphenol, 3-amino-2-hydroxypyridine, 1,3-bis-(2,4-diaminophenoxy)propane, 2,7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 1-methoxy-2-amino-4-beta-hydroxy-ethylaminobenzene (Lehmann's Blue), 2,4-diaminophenoxyethanol, 5-amino-4-chloro-o-cresol, 2,4-dichloro-m-aminophenol, 2,6-dihydroxy-3,4-dimethylpyridine and/or a physiologically acceptable salt of these compounds.

Equally preferred agents as contemplated herein are exemplified in that they contain the at least one coupling component and/or their physiologically acceptable salts in a proportion by weight of from about 0.001 to about 5.0% by weight, more preferably from about 0.025 to about 2.5% by weight, particularly preferably from about 0.05 to about 2% by weight and in particular from about 0.1 to about 1.5% by weight, respectively with respect to the total weight of the ready-to-use agent.

In order to obtain a balanced and subtle nuance formation, as contemplated herein, it is advantageous for the agent as contemplated herein to contain further colour-producing components.

It may therefore by advantageous in the present disclosure for the agent as contemplated herein or used in the method as contemplated herein to contain at least one further colour-producing component which is selected from additional oxidative dye precursors of the developer type and/or from direct dyes.

Preferred further developer components are selected from at least one compound from the group formed by p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3- diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as the physiologically acceptable salts of these compounds. Particularly preferred additional developer components in this case are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)-pyrazole, as well as their physiologically acceptable salts.

The developer components are preferably used in a quantity of from about 0.0001 to about 10% by weight, preferably from about 0.001 to about 5% by weight, respectively with respect to the ready-to-use agent.

In summary, preferred colouring agents as contemplated herein or used in the method as contemplated herein contain, respectively with respect to their weight, from about 0.05 to about 5% by weight, preferably from about 0.1 to about 4.5% by weight, more preferably from about 0.15 to about 4% by weight, yet more preferably from about 0.2 to about 3.5% by weight and in particular from about 0.25 to about 3% by weight of oxidative dye precursors.

Instead of oxidative dye precursors or as a complement thereto, the colouring agents as contemplated herein or used in the method as contemplated herein may contain at least one direct dye. These are dyes which are taken up directly by the hair and do not require an oxidative process in order to produce the colour. Direct dyes are usually nitrophenylenediamines, nitroaminophenols, azo dyes, anthraquinones or indophenols.

The direct dyes are preferably respectively used in a quantity of from about 0.001 to about 20% by weight, in particular from about 0.05 to about 5% by weight, respectively with respect to the entire ready-to-use preparation. The total quantity of direct dyes is preferably at most about 3% by weight.

Direct dyes can be classified into anionic, cationic and non-ionic direct dyes, which are selected and used by the person skilled in the art as a function of the requirements of the carrier.

Preferred anionic direct dyes are those compounds known by the international designations or trade names Bromophenol Blue, Tetrabromophenol Blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 as well as Yellow 87, Basic Orange 31 and Basic Red 51.

Particularly suitable non-ionic direct dyes are non-ionic nitro and quinone dyes and neutral azo dyes. Preferred non-ionic direct dyes are those known by the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid, and their salts, 2-amino-6-chloro-4-nitrophenol, 4-ethylamino-3-nitrobenzoic acid and 2-chloro-6-ethylamino-4-nitrophenol.

The agents as contemplated herein or used in the method as contemplated herein may also contain natural analogue dyes. Compositions as contemplated herein which contain precursors of natural analogue dyes are preferably used as air-oxidative colouring agents. In this embodiment, as a consequence, said compositions are not mixed with an additional oxidizing agent prior to use.

The dye precursors of natural analogue dyes are preferably respectively used in a quantity of from about 0.001 to about 5% by weight with respect to the ready-to-use preparation as a whole. Derivatives of 5,6-dihydroxyindoline, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline as well as 5,6-dihydroxyindolin-2-carboxylic acid, as well as derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, as well as physiologically acceptable salts of the aforementioned compounds are particularly suitable precursors of natural analogue hair dyes.

In summary, preferred colouring agents as contemplated herein or used in the method as contemplated herein are those which contain from about 0.05 to about 5% by weight, preferably from about 0.1 to about 4.5% by weight, more preferably from about 0.15 to about 4% by weight, yet more preferably from about 0.2 to about 3.5% by weight and in particular from about 0.25 to about 3% by weight of direct dye(s).

The agents as contemplated herein or used in the method as contemplated herein contain from about 0.1 to about 5% by weight, respectively calculated with respect to the undissociated dicarboxylic acid and with respect to the weight of the colouring agent, of dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this(these) acid(s).

Preferred dicarboxylic acids containing from about 2 to about 10 carbon atoms as contemplated herein are selected from malic acid, D-tartaric acid, L-tartaric acid, meso-tartaric acid, racemic acid, as well as mixtures of these acids. Malic acid is particularly preferred as contemplated herein. The dicarboxylic acids mentioned above make a considerable contribution to reducing damage to the hair by the colouring agent as contemplated herein.

Depending on the pH of the colouring agent or of the compositions used in a colouring method as contemplated herein, the at least one dicarboxylic acid containing from about 2 to about 10 carbon atoms may be present as the undissociated acid, partially dissociated acid or completely dissociated acid. If the at least one dicarboxylic acid containing from about 2 to about 10 carbon atoms is partially dissociated or completely dissociated, then the counter-ion is selected from physiologically acceptable cations such as, in particular, alkali metal, alkaline-earth metal and zinc ions, as well as ammonium ions, alkylammonium ions, alkanolammonium and glucammonium ions, in particular the mono-, di- and trimethyl-, -ethyl- and -hydroxyethylammonium ions. Salts of the saturated dicarboxylic acids containing from about 2 to about 10 carbon atoms with amin-$C_1$-$C_6$ alkanols, in particular with monoethanolamine, and amino-$C_1$-$C_6$ alkanediols, in particular with 2-amino-2-methylpropan-1-ol, 2-amino-2-methylpropan-1,3-diol, 2-aminopropan-1-ol, 3-aminopropan-1-ol, 1-aminopropan-2-ol (MIPA) and 2-amino-2-(hydroxymethyl)propan-1,3-diol (TRIS) are also preferred, wherein the salts with monoethanolamine, 2-amino-2-methylpropan-1-ol and 2-amino-2-methylpropan-1,3-diol are particularly preferred.

Exceedingly preferably, sodium, potassium, magnesium, ammonium and monoethanol-ammonium ions are used as the counter-ions for the partially or completely dissociated dicarboxylic acids containing from about 2 to about 10 carbon atoms. However, in addition, dicarboxylic acids containing from about 2 to about 10 carbon atoms neutralized with amino acids that react with alkalis such as, for example, arginine, lysine, ornithine and histidine, may also be used.

Sodium, potassium, ammonium, monoethanolammonium, lysine as well as arginine salts as well as mixtures thereof are preferred salts of the dicarboxylic acids containing from about 2 to about 10 carbon atoms.

Preferred colouring agents in accordance with the present disclosure contain the at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid or one or more salts thereof in a total quantity of from about 0.2 to about 4% by weight, preferably from about 0.33 to about 3% by weight, particularly preferably from about 0.5 to about 2% by weight, respectively calculated with respect to the undissociated dicarboxylic acid and with respect to the weight of the colouring agent.

In addition, when the dicarboxylic acids are in the form of a salt, the quantities given above are with respect to the respective dicarboxylic acid in the undissociated form, so that the quantities given are not falsified by the different molecular weights of the salts.

In summary, preferred colouring agents as contemplated herein or used in the method as contemplated herein are those in which the at least one dicarboxylic acid containing from about 2 to about 10 carbon atoms is selected from malic acid, D-tartaric acid, L-tartaric acid, meso-tartaric acid, racemic acid, alpha-ketoglutaric acid, beta-ketoglutaric acid and oxaloacetic acid as well as mixtures of these acids, preferably selected from malic acid.

Colouring agents as contemplated herein or used in the method as contemplated herein which are particularly preferred are those which contain at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, in a total quantity of from about 0.2 to about 4% by weight, preferably from about 0.33 to about 3% by weight, particularly preferably from about 0.5 to about 2% by weight, respectively calculated with respect to the undissociated dicarboxylic acid and with respect to the weight of the colouring agent as contemplated herein More particularly preferred colouring agents as contemplated herein or used in the method as contemplated herein contain, respectively calculated with respect to the undissociated dicarboxylic acid and with respect to the weight of the colouring agent, from about 0.2 to about 4% by weight, preferably from about 0.33 to about 3% by weight, particularly preferably from about 0.5 to about 2% by weight of malic acid.

The colouring agents as contemplated herein or used in the method as contemplated herein contain from about 20 to about 95% by weight of water. Preferred agents contain from about 30 to about 90% by weight, particularly preferably from about 40 to about 85% by weight, extremely preferably from about 45 to about 82.5% by weight and in particular from about 40 to about 80% by weight of water, respectively with respect to the total weight of the colouring agent as contemplated herein.

The colouring agents as contemplated herein or used in the method as contemplated herein contain less than about 0.1% by weight of peroxy compound(s). Surprisingly, hair colorants produced from agents as contemplated herein by adding oxidizing agent preparations ("developers") are more effective as regards protecting the fibres compared with those which are obtained from conventional colour creams, developers and a subsequent admixing of the dicarboxylic acid(s), for otherwise equal quantities used.

Preferably, the colouring agents as contemplated herein or used in the method as contemplated herein are formulated with even less peroxide. Particularly preferred colouring agents as contemplated herein or used in the method as contemplated herein contain less than about 0.01% by weight, preferably less than about 0.005, particularly preferably less than about 0.001% by weight of peroxy compounds and in particular are free from peroxy compounds.

Particularly preferred colouring agents as contemplated herein or used in the method as contemplated herein contain less than about 0.01% by weight, preferably less than about 0.005, preferably less than about 0.001% by weight of hydrogen peroxide (calculated as about 100% $H_2O_2$). More particularly preferred agents are completely free from hydrogen peroxide.

Particularly preferred colouring agents as contemplated herein or used in the method as contemplated herein contain less than about 0.01% by weight, preferably less than about 0.005, particularly preferably less than about 0.001% by weight of potassium, sodium and/or ammonium persulphate. More particularly preferred agents are completely free from persulphates.

The colouring agents as contemplated herein or used in the method as contemplated herein preferably contain at least one amino acid with formula (I)

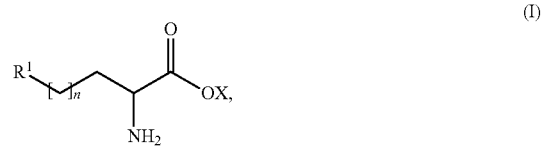

(I)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —CONH$_2$, a 1H-indol-3-yl group, a thiol group —SH and a methylsulphanyl group —SCH3, or at least one salt of this amino acid.

These amino acids provide the colouring agents as contemplated herein or used in the method as contemplated herein with ayet more improved fibre-protecting action.

Preferred amino acids with formula (I) are selected from arginine, lysine, histidine, asparagine, glutamine, cysteine, methionine, tryptophan as well as mixtures thereof. Particularly preferred colouring agents contain mixtures of arginine and lysine or at least one salt of these amino acids. Preferred colouring agents as contemplated herein contain the at least one amino acid with formula (VI) or one or more salts thereof in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring agent. Further particularly preferred colouring agents as contemplated herein contain mixtures of arginine and lysine or at least one salt of these amino acids in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring agent as contemplated herein.

Extremely preferred colouring agents as contemplated herein or used in the method as contemplated herein additionally contain at least one amino acid from the group arginine, lysine, histidine, asparagine, glutamine, cysteine, methionine, tryptophan as well as mixtures thereof, particularly preferably mixtures of arginine and lysine, in a total quantity of from about 0.05 to about 3% by weight, preferably from about 0.1 to about 2% by weight, particularly preferably from about 0.2 to about 1.2% by weight, respectively calculated with respect to the undissociated acid and with respect to the weight of the colouring agent.

Further, it has surprisingly been discovered that the reduced hair damaging action of the colouring agents as contemplated herein or used in the method as contemplated herein can be further supported when at least one compound with general formula (II) is present.

Preferred colouring agents as contemplated herein or used in the method as contemplated herein therefore additionally contain at least one compound with general formula (II)

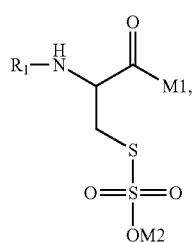

(II)

wherein

R1 represents a hydrogen atom or a structural element with formula (IV)

(IV)

wherein x represents a whole number from about 1 to about 100, the residue R2 in each of the structural elements with formula (IV) can respectively be selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group —OM2 or a structural element with formula (V)

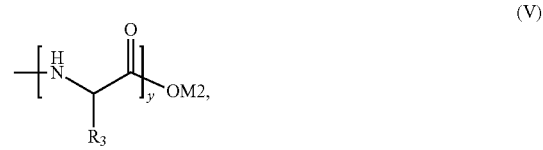

(V)

wherein y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion (NH$_4$)*, wherein preferably, one or more compounds with the aforementioned formula (II) is present in a total quantity of from about 0.001 to about 2.5% by weight more preferably from about 0.01 to about 1.0% by weight and particularly preferably from about 0.02 to about 0.1% by weight, respectively with respect to the weight of the colouring agent as contemplated herein.

The optional compounds with formula (II) include the Bunte salt of an amino acid, an oligopeptide or a peptide.

The residue R1 can either represent a hydrogen atom or a structural element with formula (IV)

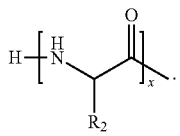
(IV)

The structural element with formula (IV) is furthermore exemplified by the number of repeat units x, wherein x represents a whole number from about 1 to about 100. The number of repeat units x indicates how many structural elements with formula (IV) are contained in the compound with formula (II).

Preferably, x represents a whole number from about 1 to about 50; more preferably, x represents a whole number from about 1 to about 20, and more particularly preferably, x represents a whole number from about 1 to about 10.

As an example, when x represents the number 10, the compound with formula (II) contains 10 structural elements with formula (IV).

In this regard, it is essential that the residue R2 in each of the structural elements with formula (IV) can respectively be selected independently of the preceding structural element with formula (IV). As an example, if the compounds with formula (II) contain 10 structural units with formula (IV), then these 10 structural units may be identical or different.

The residue R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group.

The structural element with formula (IV) is thus an amino acid which has a peptide linkage via its amino and/or its acid function within the compound with formula (II). If the amino acid is cysteine, this may also be in the form of a Bunte salt.

When the residue R2 represents a hydrogen atom, then the structural element with formula (IV) is based on the amino acid glycine. If the residue R2 is a methyl group, then the structural element with formula (IV) is based on the amino acid alanine.

In analogous manner:

| When the residue R2 represents . . . , | the structural element with formula (IV) is based on the amino acid |
|---|---|
| (H$_3$C)$_2$CH— | valine |
| (H$_3$C)$_2$CH—CH$_2$— | leucine |
| H$_3$C—CH$_2$—CH(CH$_3$) — | isoleucine |
| C$_6$H$_5$—CH$_2$— | phenylalanine |
| 4-OH—C$_6$H$_5$—CH$_2$— | tyrosine |
| HO—CH$_2$— | serine |
| H$_3$C—CH(OH)— | threonine |
| H$_2$N—CH$_2$—CH$_2$—CH$_2$—CH$_2$— | lysine |
| H$_2$N—C(NH)—NH—CH$_2$—CH$_2$—CH$_2$— | arginine |
| HOOC—CH$_2$—CH$_2$— | glutamic acid |
| HOOC—CH$_2$— | aspartic acid |
| H$_2$N—C(O)—CH$_2$—CH$_2$— | glutamine |
| H$_2$N—C(O)—CH$_2$— | asparagine |
| HS—CH$_2$— | cysteine |
| H$_3$C—S—CH$_2$—CH$_2$— | methionine |

| When the residue R2 represents . . . , | the structural element with formula (IV) is based on the amino acid |
|---|---|
| 1H-Imidazol-4-ylmethyl- | histidine |
| 1H-indole-3-ylmethyl- | tryptophan |

Finally, the residue R2 may also represent a (sulphosulphanyl)methyl group; in this case, it is a Bunte salt structure with formula HO—S(O$_2$)—S—CH$_2$—.

Depending on the pH of the colouring agent, the Bunte salt structure with formula HO—S(O$_2$)—S—CH$_2$— may also be present in its deprotonated form.

In the compound with formula (II), M1 represents the group—OM2 or a structural element with formula (V)

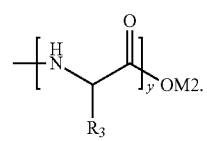
(V)

The structural element with formula (V) is exemplified by the number of repeat units y, wherein y represents a whole number from about 1 to about 100. The number of repeat units y indicates how many structural elements with formula (V) are contained in the compound with formula (II).

Preferably, y represents a whole number from about 1 to about 50; more preferably, y represents a whole number from about 1 to about 20, and more particularly preferably, y represents a whole number from about 1 to about 10.

As an example, when y represents the number 10, the compound with formula (II) contains 10 structural elements with formula (V).

In this regard, it is essential that the residue R3 in each of the structural elements with formula (V) can respectively be independently selected from the preceding structural element with formula (V). If the compounds with formula (II) contain 10 structural units with formula (V), for example, then these 10 structural units may be identical or different.

The residue R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group.

In this regard, the structural element with formula (V) may also be an amino acid, which has a peptide linkage via its amino and/or its acid function within the compound with formula (II). If the amino acid is cysteine, this may also be in the form of a Bunte salt.

| When the residue R3 represents . . . , | the structural element with formula (V) is based on the amino acid |
|---|---|
| —H | glycine |
| —CH$_3$ | alanine |

-continued

| When the residue R3 represents . . . , | the structural element with formula (V) is based on the amino acid |
|---|---|
| (H₃C)₂CH— | valine |
| (H₃C)₂CH—CH₂— | leucine |
| H₃C—CH₂—CH(CH₃)— | isoleucine |
| C₆H₅—CH₂— | phenylalanine |
| 4-OH—C₆H₅—CH₂— | tyrosine |
| HO—CH₂— | serine |
| H₃C—CH(OH)— | threonine |
| H₂N—CH₂—CH₂—CH₂—CH₂— | lysine |
| H₂N—C(NH)—NH—CH₂—CH₂—CH₂— | arginine |
| HOOC—CH₂—CH₂— | glutamic acid |
| HOOC—CH₂— | aspartic acid |
| H₂N—C(O)—CH₂—CH₂— | glutamine |
| H₂N—C(O)—CH₂— | asparagine |
| HS—CH₂— | cysteine |
| H₃C—S—CH₂—CH₂— | methionine |
| 1H-Imidazol-4-ylmethyl- | histidine |
| 1H-indole-3-ylmethyl- | tryptophan |

Finally, the residue R3 may also represent a (sulphosulphanyl)methyl group; in this case, it is a Bunte salt structure with formula HO—S(O₂)—S—CH₂—.

Depending on the pH of the colouring or bleaching agent, the Bunte salt structure with formula HO—S(O₂)—S—CH₂— may also be present in its deprotonated form.

The residue M2 represents a hydrogen atom, an equivalent of a monovalent or multivalent cation, or an ammonium ion $(NH_4)^+$.

Preferred equivalents of a monovalent or multivalent cation which may in particular be mentioned are the cations of sodium and potassium ($Na^+$ or $K^+$) or also, in fact, magnesium or calcium (½ $Mg^{2+}$ or ½ $Ca^{2+}$).

If M2 represents a hydrogen atom, then the group—OM2 is the group —OH. If M2 represents a sodium cation, then the group—OM2 is the group —ONa. If M2 represents a potassium cation, then the group—OM2 is the group —OK. If M2 represents an ammonium ion, then the group—OM2 is the group —O(NH4).

The group—OM2 is always adjacent to a carbonyl group. In summary, when M2 represents H, K, Na or ammonium, then the compound with formula (II) is either in the form of an acid in its protonated form, or in the form of the sodium, potassium or ammonium salt of that acid.

The compounds with formula (II) as contemplated herein are either the Bunte salt of the amino acid cysteine, the Bunte salts of oligopeptides, or in fact the Bunte salts of peptides.

When the residue R1 represents a hydrogen atom and the residue M1 represents a group—OM2, then the compound with formula (II) is the Bunte salt of the amino acid cysteine. In this case, the compound with formula (II) is the compound with formula (IIa),

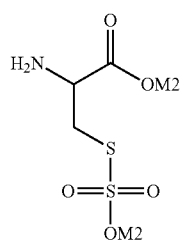

(IIa)

wherein M2 is as defined above.

If the compound with formula (IIa) is in the form of its free acid, then it is 2-amino-3-(sulphosulphanyl)propanoic acid. This substance is commercially available.

It has been shown that the use of the compound with formula (IIa) in colouring agents results in a particularly effective reduction in damage to the hair even when particularly small quantities are used, and this is still present after repeated washing of the hair. Thus, the use of compounds with formula (IIa) is particularly preferred.

In a more particularly preferred embodiment, a colouring agent as contemplated herein or used in the method as contemplated herein contains at least one compound with formula (II), wherein R1 represents a hydrogen atom and M1 represents a group—OM2.

When a compound with formula (IIa) is used, this preferably involves a use of this specific compound. However, if the Bunte salts of oligopeptides are used as the compounds with formula (II), then the colouring agent as contemplated herein may also contain several compounds with formula (II) as a mixture of different oligopeptides. These oligopeptides are defined by their average molecular weight. The average molecular weight $M_w$ of the at least one oligopeptide with formula (II) may, for example, be determined by gel permeation chromatography (GPC) with polystyrene as the internal standard.

The molecular weight of the compound with formula (II) used as contemplated herein may vary as a function of the number of structural elements with formula (IV) and/or (V) in the compound with formula (II), and as a function of the type of these amino acids. Particularly preferably as contemplated herein, the compound with formula (II) is an oligopeptide which has a molecular weight $M_w$ of from about 200 to about 2000 Da, preferably from about 250 to about 1500 Da, preferably from about 300 to about 1200 Da, in particular from about 400 to about 800 Da.

In the context of the present disclosure, the term "oligopeptide" should be understood to mean condensation products of amino acids which have the molecular weights given above.

In a more particularly preferred embodiment, a colouring agent as contemplated herein contains at least one compound with formula (II) which has a molecular weight $M_w$ of from about 200 to about 2000 Da (Dalton), preferably from about 250 to about 1500 Da, preferably from about 300 to about 1200 Da, in particular from about 400 to about 800 Da.

If a mixture of oligomers is used in the colouring agent as contemplated herein, then these mixtures may be defined by their average molecular weight.

In this case, a preferred colouring agent as contemplated herein contains at least a mixture of compounds with formula (II) which has an average molecular weight $M_w$ of from about 200 to about 2000 Da, preferably from about 250 to about 1500 Da, preferably from about 300 to about 1200 Da, in particular from about 400 to about 800 Da.

Furthermore, it has been shown that the protective or repair effect which the compounds with formula (II) exhibit also depends on the number of repeat units x and y. As described above, particularly preferably, x represents a whole number from about 1 to about 10, and y represents a whole number from about 1 to about 10.

In a further more particularly preferred embodiment, a colouring or bleaching agent as contemplated herein contains at least one compound with formula (II), wherein
R1 represents a structural element with formula (IV), and
M1 represents a structural element with formula (V), and
x represents a whole number from about 1 to about 10, and
y represents a whole number from about 1 to about 10.

In addition to the molecular weight of the compound with formula (II), the proportion of the Bunte salt units contained in the compound with formula (II) has a decisive influence on the effectiveness of the protective action or "repairing action" of the compounds.

Compounds with at least one Bunte salt unit—as is the case, for example, in the compound with formula (IIa)—are highly effective, in particular when they are used as the monomeric compound. Oligopeptides with at least one Bunte salt unit are particularly effective when they have a low molecular weight of up to about 1200, in particular about 800 Dalton.

When using oligopeptides, however, it is of particular advantage for the compound with formula (II) to have at least two, preferably at least three Bunte salt units.

In a further most particularly preferred embodiment, a colouring agent as contemplated herein contains at least one compound with formula (II), wherein
R1 represents a structural element with formula (IV), and
the residue R2 in at least one structural element with formula (IV) represents a (sulphosulphanyl)methyl group (i.e. a group HO—S($O_2$)—S—$CH_2$—).

In a further more particularly preferred embodiment, a colouring agent as contemplated herein contains at least one compound with formula (II), wherein
R1 represents a structural element with formula (IV), and
x represents a whole number of at least about 3, and
the residue R2 in at least about 3 structural elements with formula (IV) represents a 2-carboxyethyl group (i.e. a group HOOC—$CH_2$—$CH_2$—).

In a further more particularly preferred embodiment, a colouring agent as contemplated herein contains at least one compound with formula (II), wherein
M1 represents a structural element with formula (V), and
y represents a whole number of at least 3, and
the residue R3 in at least about 3 structural elements with formula (IV) represents a group (Glu).

The at least one compound with formula (II) is—with respect to the total weight of the colouring agent as contemplated herein—present in a total quantity of from about 0.001 to about 10% by weight.

Surprisingly, however, it has been shown that even when used in small concentrations, the compound(s) with formula (II) can achieve a very good reduction in damage to the hair. For this reason, it is particularly advantageous for the preferred colouring agent as contemplated herein to contain one or more compounds with the formula (II) defined above in a total quantity of from about 0.001 to about 2.5% by weight, more preferably from about 0.01 to about 1.0% by weight and particularly preferably from about 0.02 to about 0.1% by weight, respectively with respect to the weight of the colouring agent as contemplated herein.

In a further more particularly preferred embodiment, a colouring agent as contemplated herein contains one or more compounds with the formula (II) described above in a total quantity of from about 0.001 to about 2.5% by weight, more preferably from about 0.01 to about 1.0% by weight and particularly preferably from about 0.02 to about 0.1% by weight, respectively with respect to the weight of the colouring agent as contemplated herein.

Furthermore, it has surprisingly been shown that the reduced damaging action to the hair of the colouring agents as contemplated herein or used in the method as contemplated herein can be further supported when they contain specific polymers.

Preferred colouring agents as contemplated herein or used in the method as contemplated herein thus additionally contain at least one polymer A which comprises at least ten constituent units with formula (I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
wherein the at least one polymer A with at least ten constituent units with formula (I) is preferably present in a total quantity of from about 0.2 to about 5% by weight, particularly preferably from about 0.5 to about 3% by weight, extremely preferably from about 1.0 to about 2.3% by weight, respectively with respect to the weight of the colouring agent.

The term "polymer" as used in the present application should be understood to mean polymers within the meaning of the IUPAC definition, comprising at least about 10 identical constituent units.

The number of constituent units in a polymer is known as the degree of polymerization. Preferred polymers A of the present disclosure each have a degree of polymerization in the range from about 40 to about 1000, preferably from about 100 to about 800, particularly preferably from about 350 to about 650. Further preferred polymers A of the present disclosure with at least ten constituent units with formula (I) contain from about 40 to about 1000, preferably from about 100 to about 800, particularly preferably from about 350 to about 650 identical constituent units with formula (I).

Preferably $R^1$ and $R^2$, respectively independently of each other, represent hydrogen or a $C_2$-$C_{10}$ acyl group preferably selected from an acetyl, propanoyl or n-butanoyl group, particularly preferably selected from an acetyl group.

Preferred polymers A of the present disclosure contain at least about 10 constituent units with formula (I), in which X represents nitrogen, wherein the polymer A contains no permanently ionic constituent units.

Further particularly preferred polymers A of the present disclosure comprise at least about 10 constituent units with formula (I), in which X represents nitrogen and $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group.

When $R^1$ and $R^2$ together with X form a five- or six-membered, saturated or unsaturated ring, which optionally contains further heteroatoms, which are preferably selected from N and O, then this ring is preferably substituted with at least one functional group which is selected from =O. A particularly preferred X, $R^1$, $R^2$ substituent combination is a pyrrolidone group, so that in a particularly preferred constituent unit as contemplated herein with formula (I), the unit has formula (Ia),

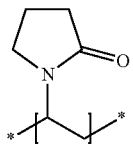

(Ia)

in which X represents nitrogen and $R^1$ and $R^2$ together with this nitrogen atom forms a five-membered saturated ring which contains no other heteroatoms and which is substituted in the 2-position with a functional group =O.

A further particularly preferred X, $R^1$, $R^2$ substituent combination is an ε-caprolactam group, so that in a particularly preferred constituent unit of the present disclosure with formula (I), the unit has formula

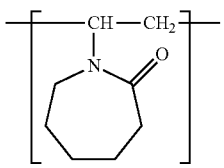

(Ib)

in which X represents nitrogen and $R^1$ and $R^2$ together with this nitrogen atom forms a six-membered saturated ring which contains no other heteroatoms and which is substituted with a functional group =O.

A further particularly preferred X, $R^1$, $R^2$ substituent combination is an imidazole group, so that a further particularly preferred unit as contemplated herein with formula (I) is a unit in which X represents nitrogen and $R^1$ and $R^2$ together with this nitrogen atom form a five-membered unsaturated ring which contains nitrogen as a further heteroatom.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen, wherein the polymer A contains no permanently ionic constituent units.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen and $R^1$ and $R^2$ together with X form a five- or six-membered, saturated or unsaturated ring which optionally contains further heteroatoms which are selected from N and O and optionally substituted with at least one C1-C6 alkyl group and/or with at least one functional group, wherein the polymer A contains no permanently ionic constituent units.

Particularly preferred polymers A of the present disclosure comprise from about 98 to about 100 mol % constituent units with formula (Ia), wherein the polymer A contains no permanently ionic constituent units.

Even more particularly preferred polymers A of the present disclosure comprise from about 98 to about 100 mol % constituent units with formula (Ia) and have a degree of polymerization in the range from about 40 to about 1000, preferably from about 100 to about 800, particularly preferably from about 350 to about 650, wherein the polymer A contains no permanently ionic constituent units. Particularly preferred polymers A are polyvinylpyrrolidone homopolymers with a degree of polymerization in the range from about 40 to about 1000, preferably from about 100 to about 800, particularly preferably from about 350 to about 650.

A further particularly preferred X, $R^1$, $R^2$ substituent combination is a constituent unit with formula (I), in which X represents oxygen, p is zero and $R^1$ represents hydrogen.

A further particularly preferred X, $R^1$, $R^2$ substituent combination is a constituent unit with formula (I), in which X represents oxygen, p is zero and $R^1$ represents an acetyl group.

Further preferred polymers A of the present disclosure contain from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), including from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 65 to about 25 mol % constituent units with formula (Ia) and from about 35 to about 75 mol % constituent units with formula (I), in which X represents oxygen, p is zero and $R^1$ represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), including from about 65 to about 25 mol % constituent units with formula (Ia) and from about 35 to about 75 mol % constituent units with formula (I), in which X represents oxygen, p is zero and $R^1$ represents an acetyl group, wherein the polymer A contains no permanently ionic constituent units.

The at least one polymer A with at least ten constituent units with formula (I) does not comprise any permanent ionic charges. However, it is possible for the constituent units with formula (I) which are present to be ionic, in particular cationic, for example by protonation of the nitrogen atom in an acidic support. However, these charges are not permanent, but rather are temporary, as they are dependent on the surrounding medium.

Preferred colouring agents as contemplated herein contain the at least one polymer A with at least ten constituent units with formula (I) in a total quantity of from about 0.2 to about 5% by weight, preferably from about 0.5 to about 3% by weight, particularly preferably from about 1.0 to about 2.3% by weight, respectively with respect to the weight of the colouring agent.

As a further optional ingredient, preferred colouring agents contain at least one permanently cationic polymer B.

Preferably, in addition to at least one permanently cationically charged monomer type, the permanently cationic polymer also contains at least one permanently anionically charged monomer type, wherein the cationic monomers are present in a molar excess with respect to the anionic monomers, so that the at least one second polymer as contemplated herein has a net cationic charge. Preferred polymers as contemplated herein of this type are known as amphoteric or zwitterionic polymers.

In a first preferred embodiment, colouring or bleaching agents as contemplated herein contain at least one permanently cationic polymer which is selected from
cationic polymers which are produced from monomers with quaternary ammonium groups with general formula (a),

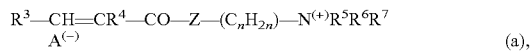

(a), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and $A^{(-)}$ represents the anion of an inorganic or organic acid,
preferably selected from cationic polymers which are produced from acrylamidopropyl trimethylammonium chloride,
particularly preferably selected from amphoteric polymers with a net cationic charge, which are produced by polymerization of
a) cationic monomers with quaternary ammonium groups with general formula (a),

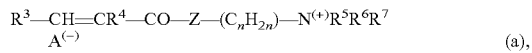

(a), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and $A^{(-)}$ represents the anion of an inorganic or organic acid, and
b) at least one unsaturated carboxylic acid selected from acrylic acid, methacrylic acid and crotonic acid, as well as mixtures of these acids, wherein the at least one unsaturated carboxylic acid may be in the form of their salts,
wherein in the polymer, the cationic monomers are present in a molar excess with respect to the anionic monomers;
extremely preferably selected from amphoteric polymers with a net cationic charge which contain the at least one monomer type with general formula (a) and the at least one unsaturated carboxylic acid monomer type selected from acrylic acid, methacrylic acid and crotonic acid, as well as mixtures thereof, in a molar ratio of from about 60:40 to about 95:5, preferably from about 75:25 to about 90:10 with respect to each other, extremely preferably selected from amphoteric copolymers with a net cationic charge which includes acrylamidopropyl trimethylammonium chloride and acrylic acid in a molar ratio of from about 60:40 to about 95:5, preferably from about 75:25 to about 90:10 with respect to each other;

2-[2-hydroxy-3-(trimethylammonio)propoxy]ethylcellulose ether chloride which, for example, is available under the INCI name polyquaternium-10, terpolymers formed from acrylic acid, diallyldimethylammonium chloride and acrylamide which, for example, are available under the INCI name polyquaternium-39, homopolymers formed from N,N,N-trimethyl-2-[(methyl-1-oxo-2-propenyl)oxy]ethanaminium chloride which, for example, are available under the INCI name polyquaternium-37, copolymers formed from diallyldimethylammonium chloride and acrylic acid which, for example, are available under the INCI name polyquaternium-22, hydroxyethylcellulose-dimethyldiallylammonium chloride copolymers which, for example, are available under the INCI name polyquaternium-4, copolymers formed from acrylamide and beta-methacrylyloxyethyltrimethylammonium methosulphate which, for example, are available under the INCI name polyquaternium-5, homopolymers of N,N-dimethyl-N-2-propenyl-2-propen-1-aminium chloride which, for example, are available under the INCI name polyquaternium-6, copolymers formed from diallyldimethylammonium chloride and acrylamide which, for example, are available under the INCI name polyquaternium-7, copolymers formed from vinylpyrrolidone and dimethylaminoethylmethacrylate diethylsulphate which, for example, are available under the INCI name polyquaternium-11, as well as mixtures of the said polymers.

Extremely preferred permanently cationic polymers as contemplated herein are selected from 2-[2-hydroxy-3-(trimethylammonio)propoxy]ethylcellulose ether chloride, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and terpolymers formed from acrylic acid, diallyldimethylammonium chloride and acrylamide, as well as binary and ternary mixtures of these polymers.

Particularly preferred polymer B mixtures contain 2-[2-hydroxy-3-(trimethylammonio)propoxy]ethylcellulose ether chloride and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain 2-[2-hydroxy-3-(trimethylammonio)propoxy]ethylcellulose ether chloride, at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and at least one terpolymer formed from acrylic acid, diallyldimethylammonium chloride and acrylamide.

Further extremely preferred permanently cationic polymers B of the present disclosure are selected from polyquaternium-10, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39, as well as binary and ternary mixtures of these polymers.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39.

Preferred colouring agents as contemplated herein contain the at least one permanently cationic polymer B in a total quantity of from about 0.05 to about 1.5% by weight, preferably from about 0.1 to about 1.0% by weight, particularly preferably from about 0.2 to about 0.8% by weight, respectively with respect to the weight of the colouring agent as contemplated herein.

The colouring preparation as contemplated herein or used in the method as contemplated herein preferably contains at least one alkalizing agent selected from ammonium hydroxide, monoethanolamine and sodium silicates, as well as mixtures thereof.

In order to achieve desired long-lasting colouring of the keratinous fibres, the colouring agent as contemplated herein must have a pH in the range from about 6.5 to about 11.0, preferably from about 8 to about 10.5, particularly preferably from about 8.5 to about 10, respectively measured at 20° C. At these pHs, the outer keratinous fibre layer opens up in an optimal manner in order to take up the oxidative dye precursors and the desired action of the peroxy compound added via the developer emulsion occurs in an optimal manner.

Preferred colouring preparations as contemplated herein or used in the method as contemplated herein have a pH in the range from about 6.5 to about 11.0, preferably from about 8 to about 10.5, particularly preferably from about 8.5 to about 10, respectively measured at 20° C.

Preferably, ammonia is used in the form of an aqueous solution. Appropriate aqueous ammonia solutions may be from about 10 to about 35 percent solutions (calculated as the % by weight; about 100 g of aqueous ammonia solution then contains from about 10 to about 35 g of ammonia). Preferably, ammonia is used in the form of a from about 20 to about 30% by weight solution, particularly preferably in the form of a about 25% by weight solution.

In a particularly preferred embodiment, the colouring agent as contemplated herein contains ammonium hydroxide in a quantity of from about 0.20 to about 2.5% by weight, preferably from about 0.5 to about 2.0% by weight, more preferably from about 1.0 to about 1.5% by weight and particularly preferably from about 0.31 to about 0.8% by weight—with respect to the total weight of the colouring agent as contemplated herein.

In addition to or instead of ammonium hydroxide, preferred colouring agents as contemplated herein contain monoethanolamine.

In order to mask the odour as far as possible and in order to optimize the fastness, the total monoethanolamine content is from about 0.2 to about 6.5% by weight, preferably from about 0.5 to about 4.0% by weight, more preferably from about 0.7 to about 2.5% by weight and particularly preferably from about 0.8 to about 1.6% by weight—with respect to the total weight of the colouring agent as contemplated herein.

The term "sodium silicates" in the context of the present disclosure means chemical compounds which are composed of sodium oxide and silicon dioxide and which can exist in a variety of molar ratios (monosilicate, metasilicate and polysilicate. An example of a sodium silicate is the sodium salt of orthosilicic acid with the empirical formula $Na_4SiO_4$, which is also known as sodium orthosilicate.

Further examples of suitable sodium silicates are the disodium metasilicate or sodium metasilicate with the empirical formula $Na_2SiO_3$, the disodium disilicate with the empirical formula $Na_2Si_2O_5$ or the disodium trisilicate with the empirical formula $Na_2Si_3O_7$.

Silicates in the amorphous form may be produced by fusing silicon dioxide and alkali oxide together in molar ratios of between from about 1:1 and about 4:1. The solids obtained in this manner are dissolved at approximately 150° C. and at a vapour pressure of 5 bar in order to obtain a solution of the sodium silicates in water; in these corresponding solutions, these are alkali soluble glasses.

Glass-like (amorphous) sodium silicates solidified from a melt or their aqueous solutions are described as alkali soluble glasses. These are also known as sodium soluble glass. Sodium soluble glasses are also included in the definition of sodium silicates within the context of this present disclosure.

The molar composition of soluble glasses is usually from about 2 to about 4 mol $SiO_2$ to about 1 mol of alkali oxide ($Na_2O$).

An example of a preferred sodium silicate is sodium soluble glass, which is in the form of an aqueous solution, has a $Na_2O$ content of from about 7.5 to about 8.8% by weight and a $SiO_2$ content of from about 25.0 to about 28.5% by weight and has the CAS No. 1344-09-5 (Chemical Abstracts Number).

Further preferred colouring agents as contemplated herein contain at least one sodium silicate in a total quantity of from about 0.1 to about 9% by weight, preferably from about 0.2 to about 8% by weight, particularly preferably from about 1 to about 7.5% by weight, respectively with respect to the total weight of the colouring agent as contemplated herein.

Furthermore, other alkalizing agents such as potassium hydroxide (KOH) and sodium hydroxide (NaOH) may be present, usually in a total quantity of from about 0.05 to about 1.5% by weight, preferably from about 0.1 to about 0.6% by weight, respectively with respect to the total weight of the colouring agent as contemplated herein.

The colouring preparation as contemplated herein or used in the method as contemplated herein furthermore optionally contains other auxiliaries and additives. In this regard, it has been shown to be advantageous in the present disclosure for the colouring preparation to contain at least one thickening agent. In principle, there are no restrictions regarding this thickening agent. Both organic as well as purely inorganic thickening agents may be employed.

If appropriate, an optional polymer A or an optional polymer B may function as the thickening agent. The thickening polymers described below are therefore encompassed in the definitions for polymer A or polymer B.

In accordance with a first preferred embodiment, the thickening agent is an anionic synthetic polymer. Preferred anionic groups are the carboxylate and sulphonate groups. Examples of anionic monomers from which the polymeric anionic thickening agent may be constituted are acrylic acid, methacrylic acid, crotonic acid, itaconic acid, maleic acid anhydride and 2-acrylamido-2-methylpropanesulphonic acid. The acidic groups here may be partially or entirely in the form of the sodium, potassium, ammonium, mono- or tri-ethanolammonium salt. Preferred monomers are maleic acid anhydride as well as, in particular, 2-acrylamido-2-methylpropanesulphonic acid and acrylic acid.

Preferred anionic homopolymers are non-crosslinked and crosslinked polyacrylic acids. Preferred crosslinking agents may be allyl ethers of pentaerythritol, sucrose and propylene. Examples of such compounds are commercially available under the trade mark Carbopol®. The homopolymer of 2-acrylamido-2-methylpropanesulphonic acid, which is commercially available under the name Rheothik®11-80, is also preferred.

In this first embodiment, it may further be preferable to use copolymers of at least one anionic monomer and at least one non-ionic monomer. Reference should be made to the substances listed above for the anionic monomers. Preferred non-ionic monomers are acrylamide, methacrylamide, acrylic acid esters, methacrylic acid esters, itaconic acid mono- and -diesters, vinylpyrrolidinone, vinyl ethers and vinyl esters.

The anionic acrylic acid and/or methacrylic acid polymerisates or copolymerisates are preferably contained in the agents as contemplated herein in a quantity of from about 0.1 to about 10% by weight, particularly preferably from about 1 to about 5% by weight, respectively with respect to the weight of the agent.

Examples of preferred anionic copolymers are copolymers formed from acrylic acid, methacrylic acid or their $C_1$-$C_6$ alkyl esters, described in the INCI declaration as Acrylates Copolymers. An example of a preferred commercial product is Aculyn® 33 from Rohm & Haas. Other preferred copolymers are formed from acrylic acid, methacrylic acid or their $C_1$-$C_6$-alkyl esters and the esters of an ethylenically unsaturated acid and an alkoxylated fatty alcohol. Particular suitable ethylenically unsaturated acids are acrylic acid, methacrylic acid and itaconic acid; particular suitable fatty alcohols are Steareth-20 or Ceteth-20. Copolymers of this type are available from Rohm & Haas under the trade mark Aculyn® 22 as well as from National Starch under the trade names Structure® 2001 and Structure® 3001.

Preferred anionic copolymers, furthermore, are acrylic acid-acrylamide copolymers as well as, in particular, polyacrylamide copolymers with monomers containing sulphonic acid groups. A particularly preferred anionic copolymer includes from about 70 to about 55 mol % acrylamide and from about 30 to about 45 mol % 2-acrylamido-2-methylpropanesulphonic acid, wherein the sulphonic acid group is partially or entirely in the form of the sodium, potassium, ammonium, mono- or triethanolammonium salt. This copolymer may also be in the crosslinked form, wherein preferred crosslinking agents are polyolefinically unsaturated compounds such as tetraallyloxyethane, allylsucrose, allylpentaerythritol and methylene-bisacrylamide. A polymer of this type is contained in the commercial products Sepigel®305 and Simulgel® 600 from SEPPIC. The use of these compounds which, in addition to the polymer component, contain a mixture of hydrocarbons ($C_{13}$-$C_{14}$ isoparaffin or isohexadecane) and a non-ionogenic emulsifier (laureth-7 or polysorbate-80), has been shown to be particularly advantageous in the context of the disclosure of the present disclosure.

Polymers produced from maleic acid anhydride and methylvinylether, in particular those which are crosslinked, are preferred thickening agents. A maleic acid-methylvinylether copolymer crosslinked with 1,9-decadiene is commercially available under the trade mark Stabileze® QM.

Preferably, the agent as contemplated herein or used in the method as contemplated herein may additionally contain at least one anionic acrylic acid and/or methacrylic acid polymerisate or copolymerisate. Known preferred polymerisates of this type are:

polymerisates formed, for example, from at least about 10% by weight acrylic acid-low alkyl ester, from about 25 to about 70% by weight methacrylic acid and, if appropriate, up to about 40% by weight of a further co-monomer, mixed polymerisates formed from about 50 to about 75% by weight ethylacrylate, from about 25 to about 35% by weight acrylic acid and from about 0 to about 25% by weight of other co-monomers. Suitable dispersions of this type are commercially available, for example under the trade mark Latekoll® D (BASF).

copolymerisates formed from about 50 to about 60% by weight ethyl acrylate, from about 30 to about 40% by weight methacrylic acid and from about 5 to about 15% by weight acrylic acid, crosslinked with ethyleneglycol dimethacrylate.

In accordance with a further embodiment, the thickening agent is a cationic synthetic polymer. Preferred cationic groups are quaternary ammonium groups. In particular, polymers in which the quaternary ammonium group is bonded via a $C_1$-$C_4$ hydrocarbon group to a main polymer chain formed from acrylic acid, methacrylic acid or derivatives thereof have been shown to be particularly suitable.

Homopolymers with general formula (HP-1),

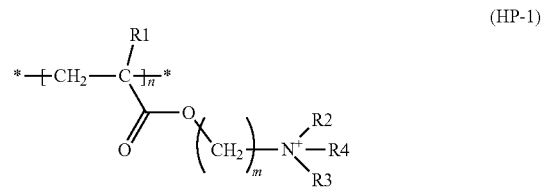

in which R1=—H or —$CH_3$, R2, R3 and R4, independently of each other, are selected from $C_1$-$C_4$ alkyl, alkenyl or hydroxyalkyl groups, m=1, 2, 3 or 4, n is a natural number and $X^-$ is a physiologically acceptable organic or inorganic anion, as well as copolymers consisting essentially of the monomer units shown in formula (HP-1), as well as non-ionogenic monomer units, are particularly preferred cationic polymer gel forming agents. In the context of these polymers, preferred polymers for the present disclosure are those for which at least one of the following conditions is valid:

R1 represents a methyl group
R2, R3 and R4 represent methyl groups
m has the value 2.

Examples of physiologically acceptable counter-ions $X^-$ which may be considered are halide ions, sulphate ions, phosphate ions, methosulphate ions as well as organic ions such as lactate, citrate, tartrate and acetate ions. Halide ions are preferred, in particular chloride.

In a further preferred embodiment, naturally available thickening agents are used. Examples of preferred thickening agents for this embodiment are non-ionic guar gums. As contemplated herein, both modified and also unmodified guar gums may be used. Unmodified guar gums are, for example, marketed under the trade mark Jaguar® C from Rhone Poulenc. Preferred modified guar gums of the present disclosure contain $C_1$-$C_6$ hydroxyalkyl groups. The hydroxymethyl, hydroxypropyl and hydroxybutyl groups are preferred. Guar gums modified in this manner are known in the art and may, for example, be produced by reaction of the guar gum with alkylene oxides. The degree of hydroxyalkylation, which corresponds to the number of alkylene oxide molecules consumed relative to the number of free hydroxyl groups in the guar gum, is preferably between from about 0.4 and about 1.2. Guar gums modified in this manner are commercially available from Rhone Poulenc under the trade marks Jaguar® HP8, Jaguar® HP60, Jaguar® HP120, Jaguar® DC 293 and Jaguar® HP105.

Further suitable thickening agents are also known in the art.

In accordance with this embodiment, furthermore, biosaccharide gums of microbial origin are preferred, such as Scleroglucan gums or xanthan gums, gums from plant exudates, such as gum *arabicum*, ghatti gum, karaya gum, tragacanth gum, carrageenan gum, agar-agar, carob bean gum, pectins, alginates, starch fractions and derivatives such as amyloses, amylopectin and dextrins, cellulose derivatives such as, for example, methylcellulose, carboxyalkylcelluloses and hydroxyalkylcelluloses.

Preferred particular hydroxyalkylcelluloses are hydroxyethylcelluloses, which are marketed under the trade name Cellosize® from Amerchol, and Natrosol® from Hercules. Suitable particular carboxyalkylcelluloses are carboxymethylcelluloses, which are marketed under the trade names Blanose® from Aqualon, Aquasorb® and Ambergum® from Hercules and Cellgon® from Montello.

Starches and their derivatives are also preferred. Starch is a storage substance in plants which in particular is present in tubers and roots, in grain and in fruit and can be obtained from a multitude of plants in high yields. The polysaccharide, which is insoluble in cold water and forms a colloidal sol in boiling water, may, for example, be obtained from potatoes, manioc, sweet potatoes, maranta, corn, cereals, rice, pulses such as, for example, peas and beans, bananas or the sap from specific types of palm (for example sago palm). Natural starches obtained from plants and/or chemically modified starches may be used in the present disclosure. A modification may, for example, be obtained by introducing different functional groups at one or more of the hydroxyl groups of the starch. Normally, it is an ester, ether or amide of the starch, if appropriate with $C_1$-$C_{40}$-substituted residues. A corn starch etherified with 2-hydroxypropyl groups such as, for example, that marketed under the trade mark Amaze®, is particularly advantageous.

Phyllosilicates (polymeric, crystalline sodium disilicates) have proved to be particularly suitable inorganic thickening agents in the context of the present disclosure. In particular, clays, especially magnesium aluminium silicate, such as bentonite, for example, in particular smectites such as montmorillonite or hectorite, which may also be suitably modified if appropriate, and synthetic phyllosilicates such as, for example, the magnesium phyllosilicate marketed by Süd Chemie under the trade mark Optigel®, are preferred.

In order to further improve the performance, in addition, $SiO_2$ compounds, optionally hydrated, may be added to the composition as contemplated herein or used in the method as contemplated herein. as contemplated herein, it may be preferable to use the optionally hydrated $SiO_2$ compounds in quantities of from about 0.05% by weight to about 15% by weight, particularly preferably in quantities of from about 0.15% by weight to about 10% by weight and more particularly preferably in quantities of from about 0.2% by weight to about 5% by weight, respectively with respect to the composition. The details regarding quantities respectively refer to the quantity of $SiO_2$ compounds (without the water fraction) in the agents.

There are essentially no restrictions as regards the optionally hydrated $SiO_2$ compounds in the context of the present disclosure. Silicas, their oligomers and polymers, as well as their salts are preferred. Preferred salts are the alkali salts, in particular the potassium and sodium salts. The sodium salts are more particularly preferred.

The optionally hydrated $SiO_2$ compounds may be present in a variety of forms. $SiO_2$ compounds in the form of silica gels or, particularly preferably, as soluble glass, are preferred in the present disclosure. A fraction of these $SiO_2$ compounds may be present in aqueous solution.

More particularly preferred as contemplated herein are soluble glasses which are formed from a silicate with formula $(SiO_2)_n(Na_2O)_m(K_2O)_p$, wherein n represents a positive rational number or 0, with the proviso that at least one of the parameters m or p is different from 0 and the ratio between n and the sum of m and p is between from about 1:4 and about 4:1. Metasilicates in which the ratio between n and the sum of m and p is about 1:2 or less are preferred.

In addition to the components described by the empirical formula, the soluble glasses may also contain small quantities of additional substances such as, for example, phosphates or magnesium salts.

Soluble glasses which are particularly preferred in the present disclosure are, inter alia, marketed by Henkel under the trade marks Ferrosil® 119, Sodium Soluble Glass 40/42, Portil® A, Portil® AW and Portil® W and from Akzo under the trade mark Britesil® C20.

Preferably, the colouring agents as contemplated herein or used in the method as contemplated herein further contain an emulsifying agent or a surfactant, wherein surface-active substances are described as surfactants or as emulsifying agents depending on their field of application and are selected from anionic, cationic, zwitterionic, amphoteric and non-ionic surfactants and emulsifying agents. These substances will be described in detail below.

Any of the anionic surface-active substances which are suitable for use on the human body are suitable as anionic surfactants in preparations as contemplated herein. These are exemplified by an anionic group which makes it soluble in water such as, for example, a carboxylate, sulphate, sulphonate or phosphate group, and a lipophilic alkyl group containing approximately 8 to about 30 C atoms. The molecule may also contain glycol or polyglycol ether groups, ester, ether and amide groups, as well as hydroxyl groups. Examples of suitable anionic surfactants are as follows, respectively in the form of the sodium, potassium and ammonium as well as the mono-, di- and trialkanol ammonium salts containing from about 2 to about 4 C atoms in the alkanol group:

linear and branched fatty acids containing from about 8 to about 30 C atoms (soaps),
  ethercarboxylic acids with formula $RO(CH_2CH_2O)_x CH_2COOH$, in which R is a linear alkyl group containing from about 8 to about 30 C atoms and x=0 or from about 1 to about 16, acylsarcosides containing from about 8 to about 24 C atoms in the acyl group, acyltaurides containing from about 8 to about 24 C atoms in the acyl group, acylisethionates containing from about 8 to about 24 C atoms in the acyl group, sulphosuccinic acid mono- and -dialkyl esters containing from about 8 to about 24 C atoms in the alkyl group and sulphosuccinic acid mono-alkylpolyoxyethylesters containing from about 8 to about 24 C atoms in the alkyl group and from about 1 to about 6 oxyethyl groups, linear alkanesulphonates containing from about 8 to about 24 C atoms, linear α-olefinsulphonates containing from about 8 to about 24 C atoms, sulphonates of unsaturated fatty acids containing from about 8 to about 24 C atoms and from about 1 to about 6 double bonds, α-sulpho-fatty acid methylesters of fatty acids containing from about 8 to about 30 C atoms, alkylsulphates and alkylethersulphates with formula $RO(CH_2CH_2O)_xSO_3H$, in which R is preferably a linear alkyl group containing from about 8 to about 30 C atoms and x=0 or from about 1 to about 12, mixtures of surface-active hydroxysulphonates, sulphated hydroxyalkylpolyethylene and/or hydroxyalkylenepropylene glycolethers, esters of tartaric acid and citric acid with alcohols, which form addition products of approximately 2 to about 15 molecules of ethylene oxide and/or propylene oxide with fatty alcohols containing from about 8 to about 22 C atoms, alkyl- and/or alkenylether phosphates with formula

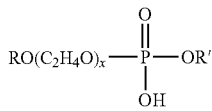

in which R preferably represents an aliphatic, optionally unsaturated hydrocarbon residue containing from about 8 to about 30 carbon atoms, R' represents hydrogen, a residue $(CH_2CH_2O)_yR$, and x and y, independently of each other, represent a number from about 1 to about 10, sulphated fatty acid alkyleneglycolesters with formula $RC(O)O(alkO)_nSO_3H$, in which R represents a linear or branched, aliphatic, saturated and/or unsaturated alkyl residue containing from about 6 to about 22 C atoms, alk represents $CH_2CH_2$, $CHCH_3CH_2$ and/or $CH_2CHCH_3$, and n represents a number from about 0.5 to about 5, monoglyceride sulphates and monoglyceride ethersulphates.

Preferred anionic surfactants are alkylsulphates, alkylethersulphates and ethercarboxylic acids containing from about 10 to about 18 C atoms in the alkyl group and up to about 12 glycol ether groups in the molecule.

Surface-active compounds which contain at least one quaternary ammonium group and at least one carboxylate, sulphonate or sulphate group in the molecule are described as zwitterionic surfactants. Particularly suitable zwitterionic surfactants are what are known as betaines, such as N-alkyl-N,N-dimethylammonium glycinates, for example cocoalkyl-dimethylammonium glycinate, N-acyl-aminopropyl-N,N-dimethylammonium glycinates, for example cocoacylaminopropyl dimethylammonium glycinate, and 2-alkyl-3-carboxymethyl-3-hydroxyethyl-imidazolines respectively containing from about 8 to about 18 C atoms in the alkyl or acyl group, as well as cocoacylaminoethylhydroxyethyl carboxymethylglycinate. A preferred zwitterionic surfactant is the fatty acid amide derivative known by the INCI name Cocamidopropyl Betaine.

Surface-active compounds which, in addition to a $C_8$-$C_{24}$ alkyl or acyl group, contain at least one free amino group and at least one —COOH— or —SO$_3$H group in the molecule and are capable of forming internal salts are known as amphoteric surfactants. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids respectively containing approximately 8 to about 24 C atoms in the alkyl group. Particularly preferred amphoteric surfactants are N-cocoalkylaminopropionate, cocoacylaminoethylaminopropionate and $C_{12}$-$C_{18}$-acylsarcosine.

Furthermore, it has been shown to be advantageous for the colouring and lightening agent to contain further, non-ionogenic surface-active substances. Non-ionic surfactants contain, as the hydrophilic group, a polyol group, a polyalkyleneglycolether group or a combination of polyol- and polyglycolether groups, for example. Examples of such compounds are:

addition products of from about 1 to about 50 mol ethylene oxide and/or from about 0 to about 5 mol propylene oxide with linear and branched fatty alcohols containing from about 8 to about 30 C atoms, such as, for example, lauryl, myristyl, cetyl, and also stearyl, isostearyl and oleyl alcohol, with fatty acids containing from about 8 to about 30 C atoms and to alkylphenols containing from about 8 to about 15 C atoms in the alkyl group, addition products closed by a methyl or $C_2$-$C_6$ alkyl end group of from about 1 to about 50 mol ethylene oxide and/or from about 0 to about 5 mol propylene oxide with linear and branched fatty alcohols containing from about 8 to about 30 C atoms, with fatty acids containing from about 8 to about 30 C atoms and with alkylphenols containing from about 8 to about 15 C atoms in the alkyl group such as, for example, those types available under the trade marks Dehydol® LS, Dehydol® LT (Cognis), polyglycerine esters and alkoxylated polyglycerine esters such as, for example, poly(3)glycerine diisostearate (commercial product: Lameform®TGI (Henkel)) and poly(2)glycerine polyhydroxy-stearate (commercial product: Dehymuls®PGPH (Henkel)).

polyol fatty acid esters such as, for example, the commercial product type Hydagen® HSP (Cognis) or Sovermol types (Cognis), higher alkoxylated, preferably propoxylated and in particular ethoxylated, mono-, di- and triglycerides such as, for example, glycerine monolaurate+20 ethylene oxides and glycerine monostearate+20 ethylene oxides, amine oxides, hydroxy mixed ethers, sorbitan fatty acid esters and addition products of ethylene oxide with sorbitan fatty acid esters such as, for example, polysorbates and sorbitan monolaurate+20 mol ethylene oxide (EO), fatty acid esters of sugars, and addition products of ethylene oxide with fatty acid esters of sugars, addition products of ethylene oxide with fatty acid alkanolamides and fatty amines, fatty acid N-alkylglucamides, alkylphenols and alkylphenolalkoxylates containing from about 6 to about 21, in particular from about 6 to about 15 carbon atoms in the alkyl chain and from about 1 to about 30 ethylene oxide- and/or propylene oxide units. Preferred examples representing this class are nonylphenol+9 EO and octylphenol+8 EO;

alkylpolyglycosides with general formula $RO-(Z)_x$, wherein R represents alkyl, Z represents sugar and x represents the number of units of sugar. The alkylpolyglycosides used in the present disclosure may contain just one specific alkyl residue R. Normally, however, these compounds originate from natural fats and oils or mineral oils. In this case, the alkyl residue R is constituted by mixtures which correspond to the starting compounds or correspond to the respective working-up of these compounds. The alkylpolyglycosides which can be used in the present disclosure contain on average from about 1.1 to about 5 units of sugar. Alkylpolyglycosides with x values of from about 1.1 to about 2.0 are preferred. Alkylpolyglycosides for which x is from about 1.1 to about 1.8 are more particularly preferred. The alkoxylated homologues of the aforementioned alkylpolyglycosides may also be used in the present disclosure. These homologues may contain an average of up to about 10 ethylene oxide and/or propylene oxide units or alkylglycoside units.

The anionic, non-ionic, zwitterionic or amphoteric surfactants are used in quantities of from about 0.1 to about 45% by weight, preferably from about 1 to about 30% by weight and more particularly preferably from about 1 to about 15% by weight, with respect to the total quantity of the ready-to-use agent.

Cationic surfactants of the quaternary ammonium compound type, esterquat and amidoamine type are also preferred in the present disclosure. Preferred quaternary ammonium compounds are ammonium halides, in particular chlorides and bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as imidazolium compounds known by the INCI names of Quaternium-27 and Quaternium-83. The long alkyl chains of the surfactants mentioned above preferably contain from about 10 to about 18 carbon atoms. Further cationic surfactants which may be used in the present disclosure are quaternized protein hydrolysates.

The alkylamidoamines are usually produced by amidation of natural or synthetic fatty acids and fatty acid fragments with dialkylaminoamines and are also exemplified by their good biodegradability, in addition to a good conditioning action. A particularly suitable compound from this group of substances which can be used in the present disclosure is constituted by the stearamidopropyldimethylamine which is commercially available under the trade mark Tegoamid® S 18.

Quaternary ester compounds, what are known as "esterquats", also have good biodegradability. Esterquats are known substances which contain both an ester function and also at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are, for example, marketed under the trade marks Stepantex, Dehyquart® and Armocare. The products Armocare® VGH-70, a N,N-bis(2-palmitoyloxyethyl)dimethylammonium chloride, as well as Dehyquart® F-75, Dehyquart® C-4046, Dehyquart® L80 and Dehyquart® AU-35, are examples of such esterquats.

The cationic surfactants are preferably present in the agents used as contemplated herein in quantities of from about 0.05 to about 10% by weight, with respect to the agent as a whole. Quantities of from about 0.1 to about 5% by weight are particularly preferred.

In a preferred embodiment, non-ionic, zwitterionic and/or amphoteric surfactants as well as mixtures thereof are preferred.

In a further preferred embodiment, the action of the colouring agents as contemplated herein or used in the method as contemplated herein may be enhanced by the use of emulsifying agents. Examples of such emulsifying agents are:

addition products of from about 4 to about 30 mol ethylene oxide and/or from about 0 to about 5 mol propylene oxide with linear fatty alcohols containing from about 8 to about 22 C atoms, with fatty acids containing from about 12 to about 22 C atoms and with alkylphenols containing from about 8 to about 15 C atoms in the alkyl group, $C_{12}$-$C_{22}$ fatty acid mono- and diesters of addition products of from about 1 to about 30 mol ethylene oxide with polyols containing from about 3 to about 6 carbon atoms, in particular with glycerine, addition products of ethylene oxide and polyglycerine to methylglucoside fatty acid esters, fatty acid alkanolamides and fatty acid glucamides, $C_8$-$C_{22}$ alkyl mono- and oligoglycosides and their ethoxylated analogues, wherein degrees of oligomerization of from about 1.1 to about 5, in particular from about 1.2 to about 2.0, and glucose as the sugar component are preferred, mixtures of alkyl-(oligo)glucosides and fatty alcohols, for example the commercially available product Montanov® 68, addition products of from about 5 to about 60 mol ethylene oxide with castor oil and hydrogenated castor oil, partial esters of polyols containing from about 3 to about 6 carbon atoms with saturated fatty acids containing from about 8 to about 22 C atoms, sterols, wherein "sterols" should be understood to mean a group of steroids which carry a hydroxyl group at C atom 3 of the steroid backbone and can be isolated both from animal tissue (zoosterols) and from plant tissue (phytosterols). Examples of zoosterols are cholesterol and lanosterol. Examples of suitable phytosterols are ergosterols, stimasterols and sitosterols. Sterols can also be isolated from fungi and yeasts; they are known as mycosterols, phospholipids, especially glucose phospholipids, which are obtained, for example, from lecithins or phosphatidylcholines, for example from egg yolk or plant seeds (for example soya beans).

fatty acid esters of sugars and sugar alcohols, such as sorbitol, polyglycerines and polyglycerine derivatives such as, for example, polyglycerine poly-12-hydroxystearate (commercial product Dehymuls® PGPH)

Linear and branched fatty acids containing from about 8 to about 30 C atoms and their Na—, K—, ammonium, Ca, Mg and Zn salts.

The agents as contemplated herein or used in the method as contemplated herein preferably contain the emulsifying agents in quantities of from about 0.1 to about 25% by weight, in particular from about 0.5 to about 15% by weight, with respect to the total quantity of the ready-to-use agent. Non-ionogenic emulsifying agents or surfactants with a HLB value of from about 10 to about 15 may be particularly preferred in the present disclosure. Of the emulsifying agent types mentioned above, emulsifying agents which do not contain any ethylene oxide and/or propylene oxide in the molecule are more particularly preferred.

The person skilled in the art will be able to select these further substances to suit the desired properties.

In the colouring method as contemplated herein, the oxidative colouring agent as contemplated herein is mixed with an oxidizing agent preparation (B) in order to form a ready-to-use agent which contains at least one peroxy compound which is preferably hydrogen peroxide, wherein the composition (B) preferably has a pH in the range from about 2.5 to about 6.5, preferably from about 3.0 to about 5.5, particularly preferably from about 3.5 to about 5.0, respectively measured at 20° C.

Preferred oxidizing agents are selected from peroxy compounds, preferably selected from hydrogen peroxide, solid addition compounds of hydrogen peroxide with inorganic or organic compounds such as sodium perborate, sodium percarbonate, magnesium percarbonate, sodium percarbamide, polyvinylpyrrolidone-n $H_2O_2$ (n is a positive whole number greater than 0), urea peroxide and melamine peroxide, furthermore selected from diammonium peroxodisulphate (also known as ammonium persulphate), disodium peroxodisulphate (also known as sodium persulphate) and dipotassium peroxodisulphate (also known as potassium persulphate), as well as mixtures of these oxidizing agents. Particularly preferred oxidizing agents used in the present disclosure are aqueous hydrogen peroxide solutions. The concentration of a hydrogen peroxide solution is determined on the one hand from the legal requirements and on the other hand from the desired effect; preferably, from about 6 to about 12% by weight solutions in water are used. Preferred oxidative colouring agents used as contemplated herein are exemplified in that the composition (B) used to produce it contains—with respect to its weight—from about 1 to about 24% by weight, preferably from about 4 to about 10% by weight, particular preferably from about 3 to about 6% by weight of hydrogen peroxide (calculated as about 100% $H_2O_2$). For oxidative hair colouring methods, usually, the colouring agent as contemplated herein, which contains one or more oxidative dye precursors and, if appropriate, one or more direct dyes, is mixed with an aqueous composition (B) containing an aqueous oxidizing agent to form the ready-to-use agent shortly before application to the hair, and then applied to the hair. Usually, the colouring agent (A) and the composition (B) containing the oxidizing agent are coordinated in a manner such that for a mixing ratio of from about 1 to about 1, with respect to the proportions by weight, a starting concentration of hydrogen peroxide in the hair colouring agent of from about 0.5 to about 12% by weight, preferably from about 2 to about 10% by weight, particularly preferably from about 3 to about 6% by weight of hydrogen peroxide (calculated as about 100% $H_2O_2$) with respect to the weight of the oxidative colouring agent is present. However, it is also possible to coordinate the colouring agent (A) as contemplated herein and the composition (B) containing the oxidizing agent in a manner such that the required concentrations in the ready-to-use oxidative colouring agent are obtained with other mixing ratios of about 1:2 or about 1:3 or even about 2:3. For a colour which requires very substantial lightening of very dark hair, the use of hydrogen peroxide or its addition products with organic or inorganic compounds is frequently not sufficient. In these cases, as a rule, a combination of hydrogen peroxide and peroxydisulphate salts (persulphate salts) is used. Preferred persulphate salts are ammonium peroxydisulphate, potassium peroxydisulphate, sodium peroxydisulphate and mixtures thereof.

The at least one persulphate salt is preferably present in a total quantity of from about 0.1 to about 25% by weight, particularly preferably in a total quantity of from about 1 to about 15% by weight, with respect to the weight of the oxidative colouring agent as contemplated herein.

Examples

The following colour creams were produced (figures as a % by weight):

| Composition | E1 | E2 | E3 | E4 |
|---|---|---|---|---|
| Water, demineralized | ad 100 | | | |
| Propanediol-1,2 | 6.0 | 6.0 | 6.0 | 6.0 |
| Cetearyl Alcohol | 9.0 | 9.0 | 9.0 | 9.0 |
| Ceteareth-20 | 2.4 | 2.4 | 2.4 | 2.4 |
| Steareth-100 | 0.6 | 0.6 | 0.6 | 0.6 |
| Paraffinum Liquidum | 2.5 | 2.5 | 2.5 | 2.5 |
| Glyceryl Monostearate | 0.5 | 0.5 | 0.5 | 0.5 |
| Sodium Sulfite Anhydrous | 0.1 | 0.1 | 0.1 | 0.1 |
| EDETA Powder | 0.5 | 0.5 | 0.5 | 0.5 |
| Hydrolyzed Wheat Protein | 0.2 | 0.2 | 0.2 | 0.2 |
| Hydrolyzed Silk Protein | 0.2 | 0.2 | 0.2 | 0.2 |
| PVP solution 30% | — | 2.0 | 2.0 | 2.0 |
| L-Arginine | 0.2 | 0.2 | 0.2 | 0.2 |
| Lysine HCl | 0.2 | 0.2 | 0.2 | 0.2 |
| Malic acid | 1.5 | 1.5 | 1.5 | 1.5 |
| D-/L-tartaric acid (racemic) | — | — | — | 0.2 |
| Vitamin C e 300 DAB | — | 0.05 | 0.05 | 0.05 |
| DC CE-8411 Smooth Plus Emulsion | — | 2.0 | 2.0 | 2.0 |
| Apricot Kernel Oil | — | 0.2 | 0.2 | 0.2 |
| Ammonia 25% | 12.0 | 12.0 | 12.0 | 12.0 |
| Fragrance | 0.5 | 0.5 | 0.5 | 0.5 |
| p-Toluylenediamine Sulphate | 0.2 | 0.2 | 0.2 | 0.2 |
| Resorcinol | 0.08 | 0.08 | 0.1 | 0.1 |
| 2-Methylresorcinol | 0.020 | 0.020 | — | — |
| 4-Chlororesorcinol | 0.02 | 0.02 | — | — |
| 2-Amino-3-hydroxypyridine | 0.009 | 0.009 | — | — |
| m-Aminophenol | 0.004 | 0.004 | 0.01 | 0.01 |
| 4-Amino-3-methylphenol | — | — | 0.02 | 0.02 |
| p-Amino-o-cresol | — | — | 0.008 | 0.008 |

| Composition | E5 | E6 | E7 | E8 |
|---|---|---|---|---|
| Water, demineralized | ad 100 | | | |
| Carbomer | 0.1 | 0.1 | 0.1 | 0.1 |
| Ammonia 25% | 12.5 | 12.5 | 12.5 | 12.5 |
| Fatty Alcohol Sulphate-Na C16-18 | 0.8 | 0.8 | 0.8 | 0.8 |
| Sodium Laureth Sulphate 27% | 5.1 | 5.1 | 5.1 | 5.1 |
| Potassium Hydroxide 50% | 1.2 | 1.2 | 1.2 | 1.2 |
| Oleic Acid | 0.4 | 0.4 | 0.4 | 0.4 |
| EDETA Powder | 0.2 | 0.2 | 0.2 | 0.2 |
| Glyceryl Monostearate | 4.6 | 4.6 | 4.6 | 4.62 |

-continued

| Composition | E5 | E6 | E7 | E8 |
|---|---|---|---|---|
| 2-Octyldodecanol | 2.3 | 2.3 | 2.3 | 2.3 |
| Cetearyl Alcohol | 13.9 | 13.9 | 13.9 | 13.9 |
| Ceteareth-20 | 3.5 | 3.5 | 3.5 | 3.5 |
| Sodium Sulfite Anhydrous | 0.1 | 0.1 | 0.1 | 0.1 |
| PVP solution 30% | 1.5 | 1.5 | — | — |
| L-Arginine | 0.2 | 0.2 | 0.2 | 0.2 |
| Lysine HCl | 0.2 | 0.2 | 0.2 | 0.2 |
| D-/L-tartaric acid (racemic) | — | 1.0 | — | — |
| Potassium tartrate (D-/L-racemate) | — | — | 1.0 | — |
| Malic acid | 1.0 | — | 1.0 | 2.0 |
| Vitamin C e 300 DAB | 0.05 | 0.05 | 0.05 | 0.05 |
| Fragrance | 0.4 | 0.4 | 0.4 | 0.4 |
| p-Toluylenediamine Sulphate | 0.1 | 0.1 | 0.1 | 0.1 |
| Resorcinol | 0.06 | 0.06 | 0.06 | 0.06 |
| 2-Methylresorcinol | 0.003 | 0.003 | 0.003 | 0.003 |
| p-Amino-o-cresol | 0.002 | 0.002 | 0.002 | 0.002 |
| 4-Amino-3-nitrophenol | 0.01 | 0.01 | 0.01 | 0.01 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A colouring agent for keratinous fibres, comprising—with respect to its weight—
    a) at least one compound selected from the group of oxidative dye precursors, direct dyes, and mixtures thereof,
    b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.1 to about 5% by weight, calculated with respect to the undissociated dicarboxylic acid and with respect to the weight of the colouring agent,
    c) from about 20 to about 95% by weight of water, and
    d) wherein the coloring agent is free from peroxy compounds.

2. The colouring agent as claimed in claim 1, comprising from about 0.05 to about 5% by weight of oxidative dye precursors.

3. The colouring agent as claimed in claim 1, wherein the at least one dicarboxylic acid comprising from about 2 to about 10 carbon atoms is malic acid.

4. The colouring agent as claimed in claim 1, wherein the at least one dicarboxylic acid comprising from about 2 to about 10 carbon atoms is present in a total quantity of from about 0.2 to about 4% by weight, calculated with respect to the undissociated dicarboxylic acid and with respect to the weight of the colouring agent.

5. The colouring agent as claimed in claim 1, further comprising at least one amino acid chosen from the group of arginine, lysine, histidine, asparagine, glutamine, cysteine, methionine, tryptophan, and mixtures thereof.

6. The colouring agent as claimed in claim 1, further comprising at least one compound with general formula (III)

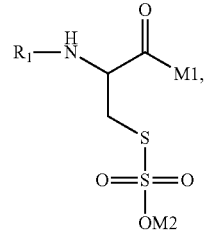

(III)

wherein
R1 represents a hydrogen atom or a structural element with formula (IV)

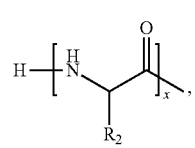

(IV)

wherein
x represents a whole number from about 1 to about 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group,
M1 represents the groun —OM2 or a structural element with formula (V)

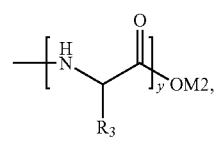

(V)

wherein
y represents a whole number from about 1 to about 100,
each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, and M2 represents a hydrogen atom, an equivalent of a monovalent or multivalent cation, or an ammonium ion $(NH_4)^{3\oplus}$.

7. The colouring agent as claimed in claim 1, further comprising at least one polymer A, which comprises at least ten constituent elements with formula (I)

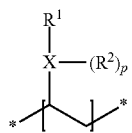

(I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are selected from N and O and/or optionally substituted with at least one C1-C6 alkyl group and/or optionally substituted with at least one functional group, and
p is equal to about 0 when X represents oxygen and p is equal to about 1 when X represents nitrogen, and
wherein the polymer A contains no permanently ionic constituent units.

8. A method for the oxidative colouring of keratinous fibres, comprising the following steps of the method
I. preparing a composition (A) comprising
a) at least one compound selected from the group formed by oxidative dye precursors, direct dyes and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.1 to about 5% by weight, respectively calculated with respect to the undissociated dicarboxylic acid and with respect to the weight of the composition (A),
c) from about 20 to about 95% by weight of water, and wherein the composition is free from peroxy compounds
II. preparing a composition (B) comprising at least one peroxy compound,
III. mixing the compositions (A) and (B) together, then immediately
IV. applying the mixture of (A) and (B) to the keratinous fibres, and
V. rinsing out after a treatment time of from about 0.1 to about 60 minutes.

9. The method as claimed in claim 8, wherein the composition (A) is a colouring agent comprising—with respect to its weight—
a) at least one compound selected from the group of oxidative dye precursors, direct dyes, and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.1 to about 5% by weight, calculated with respect to the undissociated dicarboxylic acid and with respect to the weight of the colouring agent,
c) from about 20 to about 95% by weight of water, and wherein the composition is free from peroxy compounds.

10. The colouring agent as claimed in claim 1, comprising from about 0.25 to about 3% by weight of oxidative dye precursors.

11. The colouring agent as claimed in claim 7, wherein X, $R^1$, $R^2$, and p represent an imidazole group.

12. The colouring agent as claimed in claim 1, wherein the at least one dicarboxylic acid comprising from about 2 to about 10 carbon atoms is selected from the group of ketoglutaric acid, oxaloacetic acid, and combinations thereof.

13. The colouring agent as claimed in claim 1, further comprising an amino acid selected from the group of asparagine, methionine, and combinations thereof.

14. The colouring agent as claimed in claim 6, wherein one or more compounds with the aforementioned formula (III) is present in a total quantity of 0.001 to 2.5% by weight, calculated with respect to the weight of the colouring agent.

15. The colouring agent as claimed in claim 7, wherein the at least one polymer A with at least ten constituent units with formula (I) is present in a total quantity of from about 1.0 to about 2.3% by weight, calculated with respect to the weight of the colouring agent.

16. The method of claim 8, wherein the composition (B) has a pH in the range of from about 2.5 to about 6.5.

17. A colouring agent for keratinous fibres, comprising—with respect to its weight—
a) from about 0.05 to about 5% by weight of at least one compound selected from the group of oxidative dye precursors, direct dyes, and mixtures thereof,
b) dicarboxylic acid(s) containing from about 2 to about 10 carbon atoms, selected from malic acid, D-tartaric acid, L-tartaric acid, meso-tartaric acid, racemic acid, alpha-ketoglutaric acid, beta-ketoglutaric acid and oxaloacetic acid, and/or salt(s) of this (these) acid(s), wherein the dicarboxylic acid(s) containing from about 2 to about 10 carbon atoms are present in an amount of from about 0.5 to about 2% by weight, calculated with respect to the undissociated dicarboxylic acid and with respect to the weight of the colouring agent,
c) from about 20 to about 95% by weight of water,
from about 0.2 to 1.2% by weight of at least one amino acid chosen from the group of arginine, lysine, histidine, asparagine, glutamine, cysteine, methionine, tryptophan as well as mixtures thereof,
from about 0.02 to 1.0% by weight of at least one compound with general formula (III)

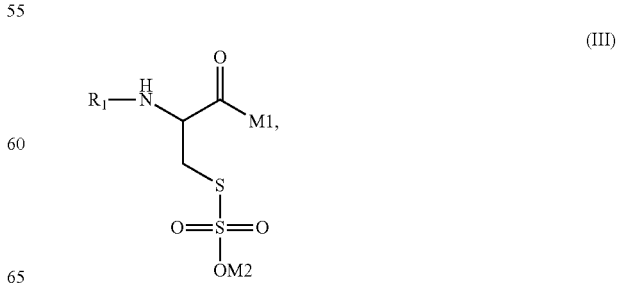

(III)

wherein

R1 represents a hydrogen atom or a structural element with formula (IV)

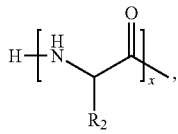
(IV)

wherein x represents a whole number from about 1 to about 100, each R2 individually represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M1 represents the group —OM2 or a structural element with formula (V)

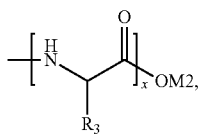
(V)

wherein y represents a whole number from about 1 to about 100, each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, and M2 represents a hydrogen atom, an equivalent of a monovalent or multivalent cation, or an ammonium ion $(NH4)^+$, and from about 1.0 to about 2.3 weight % of at least one polymer A, which comprises at least ten constituent elements with formula (I)

(I)

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are selected from N and O and/or optionally substituted with at least one C1-C6 alkyl group and/or optionally substituted with at least one functional group, and p is equal to about 0 when X represents oxygen and p is equal to about 1 when X represents nitrogen, and wherein the polymer A contains no permanently ionic constituent units, wherein the colouring agent is free from peroxy compounds.

* * * * *